United States Patent
Weiss

(10) Patent No.: US 7,999,549 B2
(45) Date of Patent: Aug. 16, 2011

(54) TRANSMISSION PATH FOR USE IN RF FIELDS PROVIDING REDUCED RF HEATING

(75) Inventor: Steffen Weiss, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 51 days.

(21) Appl. No.: 12/375,750

(22) PCT Filed: Jul. 16, 2007

(86) PCT No.: PCT/IB2007/052832
§ 371 (c)(1),
(2), (4) Date: Jan. 30, 2009

(87) PCT Pub. No.: WO2008/015605
PCT Pub. Date: Feb. 7, 2008

(65) Prior Publication Data
US 2009/0256574 A1    Oct. 15, 2009

(30) Foreign Application Priority Data
Aug. 2, 2006    (EP) .................................. 06118280

(51) Int. Cl.
*G01V 3/00*    (2006.01)
(52) U.S. Cl. ....................................... 324/322; 324/318
(58) Field of Classification Search .................. 324/322, 324/318
See application file for complete search history.

(56) References Cited

U.S. PATENT DOCUMENTS

| | | | |
|---|---|---|---|
| 5,217,010 A * | 6/1993 | Tsitlik et al. ...................... 607/9 |
| 5,638,001 A * | 6/1997 | Vrijheid et al. ............... 324/318 |
| 5,869,966 A | 2/1999 | Gatehouse |
| 6,496,714 B1 | 12/2002 | Weiss et al. |
| 6,710,597 B2 | 3/2004 | Reykowski et al. |
| 7,689,288 B2 * | 3/2010 | Stevenson et al. .............. 607/63 |
| 2005/0134277 A1 | 6/2005 | Matschl et al. |
| 2006/0148306 A1 | 7/2006 | Desinger et al. |
| 2010/0023000 A1* | 1/2010 | Stevenson et al. .............. 606/33 |

FOREIGN PATENT DOCUMENTS

DE    3815419 A1    11/1989
(Continued)

OTHER PUBLICATIONS

Umathum, R., et al.; An Actively Segmented Transmission Line for Improved MR Safety of Interventional Devices; 2006; Proc. Intl. Soc. Mag. Reson. Med.; 14:1396.

*Primary Examiner* — Louis Arana

(57) ABSTRACT

A transmission path (2) comprising an electrically conductive link or connection lead or line or cable (21) is disclosed, which path is or can be made RF safe (especially with respect to heating due to standing waves) when guided through RF electrical and/or magnetic fields especially of a MR imaging system and which is especially suitable for connecting a base or connection unit (1), like for example a power supply or a control or evaluation unit (first unit), with a distal or remote electrical unit (3) like a sensor or a detector, a transmit and/or receive unit, or an accessory device like for example an RF body or surface coil system, or an invasive or interventional device like for example a catheter or implantables (second unit), especially in a magnetic resonance (MR) imaging system. The transmission path may comprise pressure switches or optical switches.

10 Claims, 3 Drawing Sheets

FOREIGN PATENT DOCUMENTS

| | | |
|---|---|---|
| DE | 10118195 C1 | 11/2002 |
| WO | 0242790 A1 | 5/2002 |
| WO | 02074164 A1 | 9/2002 |
| WO | 03037429 A1 | 5/2003 |
| WO | 2004001434 A1 | 12/2003 |
| WO | 2004090914 A1 | 10/2004 |
| WO | 2005024868 A2 | 3/2005 |
| WO | 2005103748 A1 | 11/2005 |
| WO | 2006067703 A2 | 6/2006 |

\* cited by examiner

TRANSMISSION PATH FOR USE IN RF FIELDS PROVIDING REDUCED RF HEATING

FIELD OF THE INVENTION

The invention relates to a transmission path for use in a RF electrical and/or magnetic field especially of a MR imaging system, wherein the path comprises at least one electrically conductive link or connection lead or line or cable, for electrically connecting a first and a second electrical unit with each other, which path is or can be made RF safe (especially with respect to heating due to standing waves) when guided through the RF electrical and/or magnetic field especially of a MR imaging system. The invention further relates to a method for operating such a transmission path.

The transmission path is especially suitable for connecting a base or connection unit, like for example a power supply or a control or evaluation unit (first unit) with a distal or remote electrical unit like a sensor unit or a detector unit, a transmit and/or receive unit, or an accessory device like for example an RF body or surface coil system, or an invasive or interventional device like for example an active or passive catheter or implantables (second unit), as used in a magnetic resonance (MR) imaging system.

Furthermore, the invention relates to a connection or base unit for operating, controlling and/or supplying at least one distal or remote electrical unit via such a transmission path.

The invention as well relates to a MR compatible device, comprising a first electrical unit and a second electrical unit and a transmission path for electrically connecting both units with each other.

Finally, the invention relates to a magnetic resonance imaging system or apparatus, comprising a transmission path and/or a connection unit and/or a MR compatible device as mentioned above.

BACKGROUND OF THE INVENTION

MR imaging systems are used in particular for the examination and treatment of patients. By such a system, the nuclear spins of the body tissue to be examined are aligned by a steady main magnetic field ($B_0$ field) and are excited by RF pulses ($B_1$ field). The resulting relaxation signals are exposed to gradient magnetic fields for the purpose of localization (or slice selection) and are received and evaluated in order to form in a known manner therefrom a one-, two- or three-dimensional image of the body tissue.

Essentially two types of MR imaging systems can be distinguished. The first one is the so called open MR imaging system (vertical system) in which a patient is introduced into an examination zone which is situated between the ends of a C-arm. The patient is accessible during the examination or treatment from practically all sides. The second one is a MR imaging system which comprises a tubular (cylindrical) examination space (axial system) into which the patient is introduced.

RF coil systems are provided for the transmission of the RF pulses ($B_1$ field) and the reception of the relaxation signals. In addition to the RF coil systems which are permanently built into the MR imaging apparatus (body coils for imaging substantially the whole body of a patient), use is also made of RF surface coils which can be flexibly arranged, for example, as a sleeve or pad around or in a specific region to be examined. Similarly, RF head coils are provided and adapted for the examination of a head of a patient.

Furthermore, use is made of catheters and implantable cardiovascular devices or other invasive or interventional devices which are introduced into the patient, for example, in order to take a sample of tissue or for RF ablation of tissue during the MR imaging and which comprise at least one coil element, an oscillator or the like at least at the area of their tips for the purpose of localization in the reproduced image or for the purpose of imaging.

For connecting the above distal electrical units with a connection or base unit, notably a power supply or a control or evaluation unit (which can be a part of the related MR imaging system or a separate part) electrically conductive links or connection leads or lines or cables usually have to be guided through the above mentioned (strong) RF electrical and/or magnetic fields of the MR imaging system or MR scanner.

Especially RF fields can induce RF common mode signals (currents) in the connection line and in the surrounding body tissue of a patient. These currents involve not only the risk of disturbances or destruction of the distal and/or of the connection unit, but notably can give rise to substantial heating of the line and of the adjacent body tissue and, especially in the case of surface coils and catheters, to burning of the patient when the connection line is too close to or within the patient. Consequently, such lines have to be made RF safe with respect to these risks.

U.S. Pat. No. 6,496,714 discloses an RF safe invasive device with at least one long conductor for use in a magnetic resonance imaging apparatus. The invasive device is provided with at least one series element of controllable impedance especially in the form of a diode, incorporated into the long conductor where the impedance of the series element is controlled by a control unit such that during RF transmission the series elements subdivide the long conductor into sections substantially shorter than half the wavelength in tissue of the RF used. By this, standing RF waves along the conductor during RF transmission, and the associated dangerous heating of the device and surrounding tissue shall be avoided.

SUMMARY OF THE INVENTION

It has revealed that an invasive device as disclosed in the above U.S. Pat. No. 6,496,714 may have three major drawbacks: Firstly, subdividing the conductor by means of diodes induces the risk, that the impedance during the RF transmission (disconnected conductor sections) is not high enough in any cases or under any environmental or operational conditions, or for any RF frequencies or related high power levels of the RF transmission. Secondly, subdividing the conductor by means of diodes also requires a current to close and a reverse bias voltage to open the diodes, which has the disadvantage to limit the battery lifetime of the control unit, e.g. if applied for an implantable device. Thirdly, the use of diodes implies that there are two parallel cables required to conduct the current to and from the distal unit and to apply the reverse voltage to achieve RF safety. This complicates the transmission line unnecessarily if only a single lead would be required for signal transmission, e.g. for a unipolar signal.

Consequently, an object underlying the invention is to provide a transmission path and a method for operating such a transmission path which can be guided through strong RF electrical and/or magnetic fields without involving a considerable risk of disturbances or destructions of the connected units or of burning of a patient under a variety of environmental or operational conditions and is thus RF safe.

Another object underlying the invention is to provide a transmission path and a method for operating such a transmission path which can be guided through strong RF electrical and/or magnetic fields without involving a considerable risk of disturbances or destructions of the connected units or of burning of a patient, wherein the transmission path and the method for operating the same do require minimal electrical power so that the lifetime of a battery which is required for the operation is enhanced.

Another object underlying the invention is to provide a transmission path and a method for operating such a transmission path which can be guided through strong RF electrical and/or magnetic fields without involving a considerable risk of disturbances or destructions of the connected units or of burning of a patient also in case that the transmission path is realized in the form of one single signal lead.

Especially it is an object of the invention to provide a transmission path which is or can be made RF safe and which has a minimum loss and a high transmission quality for the signals to be transmitted over the path.

Finally, it is an object of the invention to provide a MR compatible device comprising a first electrical unit and a second electrical unit and a transmission path for electrically connecting both units with each other which device is or can be made RF safe in the sense as explained above.

At least one of the objects is solved by a transmission path comprising at least one electrically conductive link or connection lead or cable or line for electrically connecting a first and a second electrical unit with each other, and at least one switching unit comprising electrical contacts for electrically separating and connecting, respectively, at least two segments of the lead or cable or line and for providing RF safety of the line when guided through a RF electrical and/or magnetic field by opening the contacts.

Furthermore, at least one of the objects is solved by a connection or base unit as described herein, a MR compatible device as described herein, a method as described herein and a MR imaging system as described herein.

A substantial advantage of these solutions is that a transmission path is provided which by means of the electrical contacts can be opened or interrupted electrically to a low or substantially zero conductance and to a low or substantially zero capacitance in order to provide RF safety, and which can be closed or connected to a low or substantially zero impedance, each for frequencies between 0 and some GHz, in order to be used for transmitting signals and/or power.

Furthermore, electrical contacts are in most cases more reliable even under detrimental conditions than e.g. in case of switched impedance elements like diodes, so that a superior MR compatibility is obtained.

Another advantage of these solutions is that the transmission path can be used for transmitting low power RF signals as well as high power RF signals in virtually any frequency and power range, and especially in a frequency range below 1 MHz down to 1 kHz because no transformers or other elements having a frequency-dependent impedance are present in the transmission path.

The subclaims relate to advantageous embodiments of the invention.

A transmission path as described herein has an advantage, that the at least one switching unit can be switched or controlled remotely and that there is substantially no risk of disturbances by RF electrical and/or magnetic fields and no risk of the generation of standing waves and excessive temperatures (as in the case of an electrical cable for remote controlling or switching) because the pressure tube for remotely switching or controlling the at least one switching unit is a non-metallic tube.

Furthermore, the at least one switching unit can either be switched automatically e.g. by means of a sensor (which detects a RF electrical and/or magnetic field and/or a temperature, wherein a related pressure source is activated if the sensor output exceeds a predetermined threshold value), or by an external unit (e.g. a MR apparatus), or by activating a related pressure source manually by a user, e.g. before or when a RF transmission by the MR apparatus is activated.

Alternatively, instead of using a pressure tube, the switching unit can as well be provided for opening (and preferably closing as well) the contacts automatically, for example in the form of a bimetal or thermal switch which opens the contacts in case of an increasing temperature of the conductive lead or line.

An embodiment as described herein has an advantage that a compact transmission path comprising the electrically conductive lead or line, the at least one switching unit and the tube for operating the switching unit can be realized.

A connection or base units as described herein have an advantage that they can be controlled by a microcomputer by which certain environmental conditions can be evaluated in order to control the switching unit in an optimized manner.

Alternatively or additionally, the connection or base unit can be controlled externally, e.g. by a person who conducts a MR examination of a patient or by a trigger signal generated by a MR imaging system or MR scanner when RF pulses are transmitted.

An embodiment of a connection unit as described herein has an advantage that a compact unit is provided which encloses all substantial components for operating a transmission path according to the invention.

Further details, features and advantages of the invention will become apparent from the following description of preferred and exemplary embodiments of the invention which are given with reference to the drawings.

DETAILED DESCRIPTION OF PREFERRED EMBODIMENTS

Figure 1A:
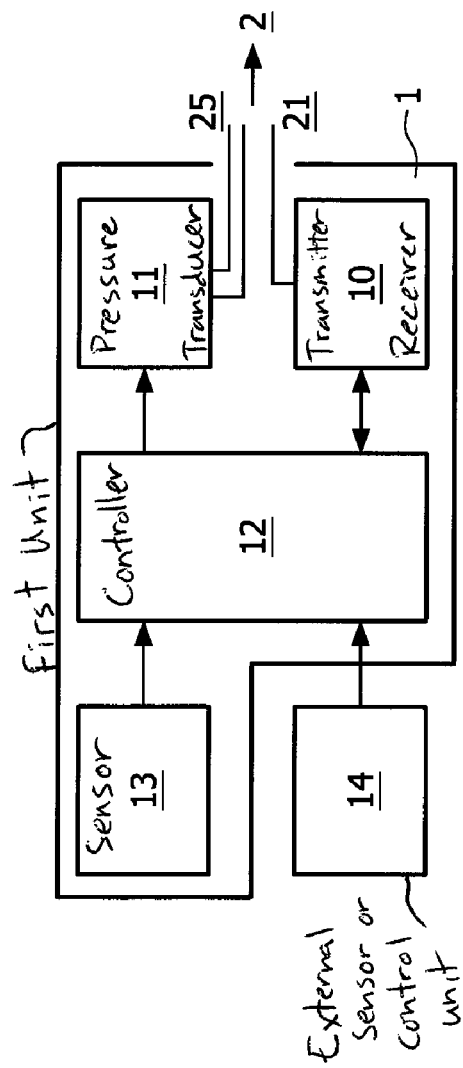
FIG. 1 shows a schematic view of an embodiment of a MR compatible device according to the invention.
Figure 1B:
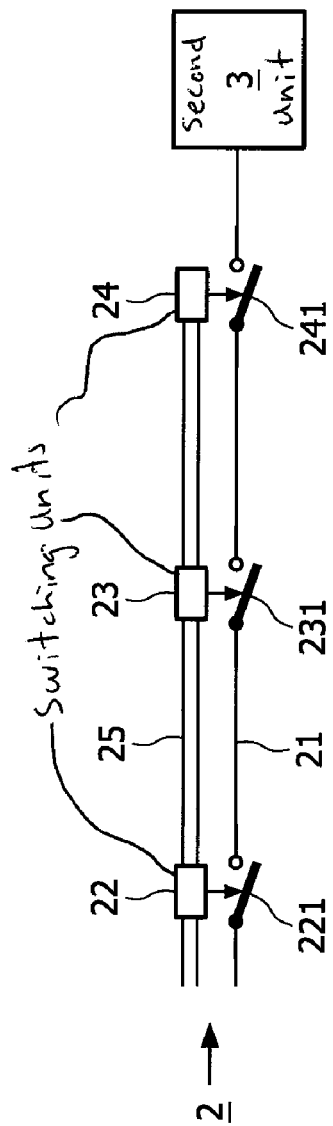

FIGS. 1A and 1B schematically show substantial components of a MR compatible device according to the invention which comprises a first electrical unit 1, a second electrical unit 3 and a transmission path 2 for electrically connecting both units 1, 3 with each other.

One example for such a MR compatible device is a cardiac pacemaker wherein the first unit 1 is a base or connection unit comprising a pulse generator, the second unit 3 is a pacing electrode, and the transmission path 2 are the pacemaker leads between the generator and the pacing electrode. Another example is an active catheter in which the second unit 3 is an MR coil for active localization at the tip of a transmit unit, which is connected via a transmission path 2 in the form of a coaxial lead to a base or connection unit (first unit 1) outside the body of a patient.

Alternatively, the connection or base unit 1 can be provided as e.g. a control or evaluation unit or a power supply unit, which is used for operating, controlling and/or supplying the second electrical unit 3 and/or for evaluating signals which are received or detected by the second electrical unit 3 by means of a corresponding control or supply means or a signal transmitter/receiver 10.

The second unit 3 is generally provided as a remote or distal unit like e.g. a sensor or a detector unit, a transmit and/or receive unit or an accessory unit like an RF body or surface coil system of an MR imaging system or an invasive or interventional unit (e.g. the distal section of a passive or active catheter for fast localization, the distal section of an electrophysiology catheter for endocardial ECG mapping, pacing, or RF ablation), or an according part of an implantable (e.g. the stimulation electrodes of a neurostimulator, an internal cardioverter or defibrillator).

The transmission path 2 comprises an electrically conductive link, lead or line or cable 21 for electrically connecting the first and the second unit 1, 3 with each other. The transmission path 2 further comprises a plurality of switching units 22, 23, 24, . . . , each comprising electrical contacts 221, 231, 241, . . . which are serially connected into the line 21 and which each separate the line 21 electrically into line segments or sections if the contacts 221, 231, 241 . . . of the switching units 22, 23, 24, . . . are open.

The switching units 22, 23, 24, . . . are preferably pressure switches in which the contacts 221, 231, 241, . . . are opened and/or closed by pressure which is supplied to the switching units by means of a medium. The medium is preferably a gaseous or liquid medium which is fed through a non-metallic pressure tube 25.

For pressurizing the medium, the first unit 1 is provided with a pressure transducer 11 which is controlled by a controller 12. The controller 12 receives output signals of at least one sensor 13 for detecting a RF electrical field and/or a magnetic field and/or a temperature, and comprises an input terminal for an external sensor or an external control unit 14 which can be a part of the MR scanner.

Furthermore, the controller 12 and the signal transmitter/receiver 10 can be provided for bidirectionally exchanging control signals between each other. The signal transmitter/receiver 10 can e.g. indicate to the controller 12 when a signal has to be transmitted over the line 21, so that the controller 12 controls the pressure transducer 11 such that it closes the contacts 221, 231, 241, . . . of the switching units 22, 23, 24, . . . . Another example is that the controller 12 can indicate to the signal transmitter/receiver 10 that a certain signal transmission over the line 21 has to be delayed or interrupted until the contacts 221, 231, 241, . . . of the switching units 22, 23, 24, . . . are closed by means of the pressure transducer 11 to allow such a transmission. A further example is to delay the transmission of a pacing pulse of a pacemaker over the line 21 by a few milliseconds until the MR system has finished an RF pulse transmission.

The at least one sensor 13 can be a magnetic field sensor, preferably reed switches, and/or an electric field sensor, preferably in the form of a RF receive antenna, and/or a known temperature sensor.

The output signals of the at least one sensor 13 are evaluated by the controller 12 with respect to the presence or strength of the detected RF electrical field and/or magnetic field and/or a value of the detected temperature, and an output signal is generated and submitted from the controller 12 to the pressure transducer 11 if according to the evaluation at least one of the detected values exceeds a predetermined threshold value.

Upon reception of such an output signal, the pressure transducer 11 operates the switching units 22, 23, 24, . . . by pressurizing the medium within the pressure tube 25 such that the contacts 221, 231, 241, . . . are opened so that the transmission path 2 is RF safe.

More in detail, the threshold value(s) can be chosen such that the electrically conductive link or line 21 is interrupted every time, the RF electric or magnetic field is generated by the related MR imaging system. Alternatively or additionally, a temperature sensor can be used which is preferably located at the transmission path 2 so that the electrically conductive link or line 21 is interrupted by opening the contacts 221, 231, 241, . . . if the temperature exceeds a predetermined threshold value.

Preferably, the controller 12 is provided such that the contacts 221, 231, 241, are opened if the sensor 13 detects that the transmission path 2 is subjected to a strong RF transmission field and a strong static magnetic field within the examination space of a MR imaging system.

As an example, the controller 12 controls the pressure transducer 11 to open all switching units 22, 23, 24, . . . if a magnetic field sensor 13 senses a field above 0.5T. As another example, the controller 12 controls the pressure transducer 11 to open all switching units 22, 23, 24 if a magnetic field sensor 13 senses a field above 0.5T and an electric field sensor (RF receive antenna, not shown in FIG. 1) detects RF transmission with a power above a predefined threshold value and/or of a frequency known to be used for MR imaging, or a frequency indicated by an external controller 14. As another example, the controller 12 opens all switching units 22, 23, 24, . . . via the pressure transducer 11 if the temperature detected by a temperature sensor rises above a predefined level of e.g. 40° C. In general, the controller 12 may be programmed to use any combination of sensor output signals to open or close the switching units 22, 23, 24, . . . .

Additionally or alternatively, the controller 12 may be supplied with an external signal generated by the external controller 14 for operating the switching units 22, 23, 24, . . . via the pressure transducer 11. One such example is an MR compatible device in the form of a catheter in which the base or connection unit 1 stays outside the body of the patient and the catheter tube including the lead 2 is within the body of the patient. The base or connection unit 1 is supplied with an external trigger signal generated by the external controller 14 (which may be a part of the MR scanner) that indicates the transmission of RF pulses by the MR scanner, so that the contacts 221, 231, 241, . . . of the switching units 22, 23, 24, . . . are opened.

In dependence on the construction and design of the connection or base unit 1, the transmission path 2 can be fixedly connected with the connection unit 1 or can be provided separably (for example by means of plugs or other separable connectors) from the connection unit 1.

According to another alternative, a switching unit in the form of an electrical relay which is supplied and/or controlled via an optical fiber (on which no standing electrical waves can be generated) could be used as well instead of a pressure switch. Furthermore, such a switching unit could comprise a detector or sensor (which is supplied via the optical fiber) for detecting an electrical or magnetic field or a temperature increase, and for opening the contacts 221, 231, 241, . . . in case of an increased electrical or magnetic field or temperature.

Figure 2:
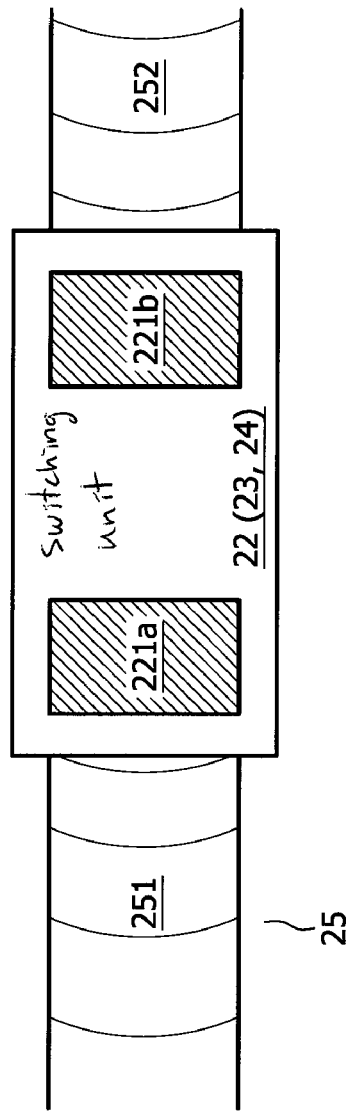
FIG. 2 shows a schematic top view of a first embodiment of a switching unit for separating and connecting the electrically conductive link.
Figure 3:
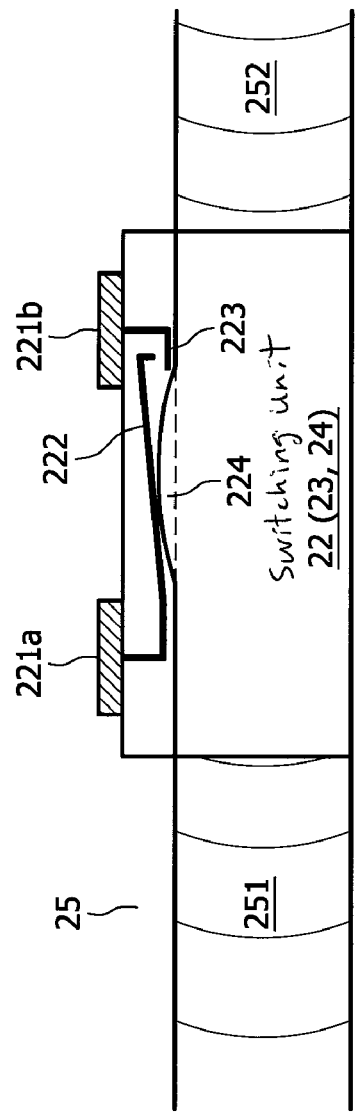
FIG. 3 shows a side view in section of FIG. 2.

FIG. 2 shows a schematic top view of a first embodiment of one of the switching units in the form of a pressure switch 22 (23, 24) between two adjacent segments or sections 251, 252 of the pressure tube 25. FIG. 3 shows a side view in section of FIG. 2.

According to these Figures the pressure switch 22 comprises a first and a second soldering pad 221a, 221b for fixing adjacent segments or sections of the electrically conductive link or line or cable 21.

The pads 221a, 221b are electrically connected with and disconnected from each other by means of a pivoted metallic lever 222 at one pad 221a and a counter contact 223 at the other pad 221b. A thin and flexible membrane 224 is positioned between the medium within the tube 25 and the lever 222. The membrane 224 can be based on an ultra thin polysilicon layer or a polymer for example a polyimide.

The lever 222 is pretensioned in an inoperative position (i.e. the pressure transducer 11 is inactive) into a contact-closed position at the counter contact 223 so that the pads 221a, 221b are electrically connected and the pressure switch 22 is closed.

If the medium within the pressure tube 25 is pressurized by means of the pressure transducer 11, the membrane 224 bulges up and lifts the lever 222 from the counter contact 223, so that the pads 221a, 221b are electrically disconnected and the pressure switch 22 is opened as indicated in FIG. 3.

In order to enhance safety of the transmission path 2 in case of a loss of pressure or a failure of the pressure transducer 11, the pressure switch 22 is preferably provided such that the lever 222 is pretensioned into a contact-open position, and the contact-closed position of the lever 222 is obtained by the pressure exerted via the pressurized medium onto the lever 222.

Figure 4:
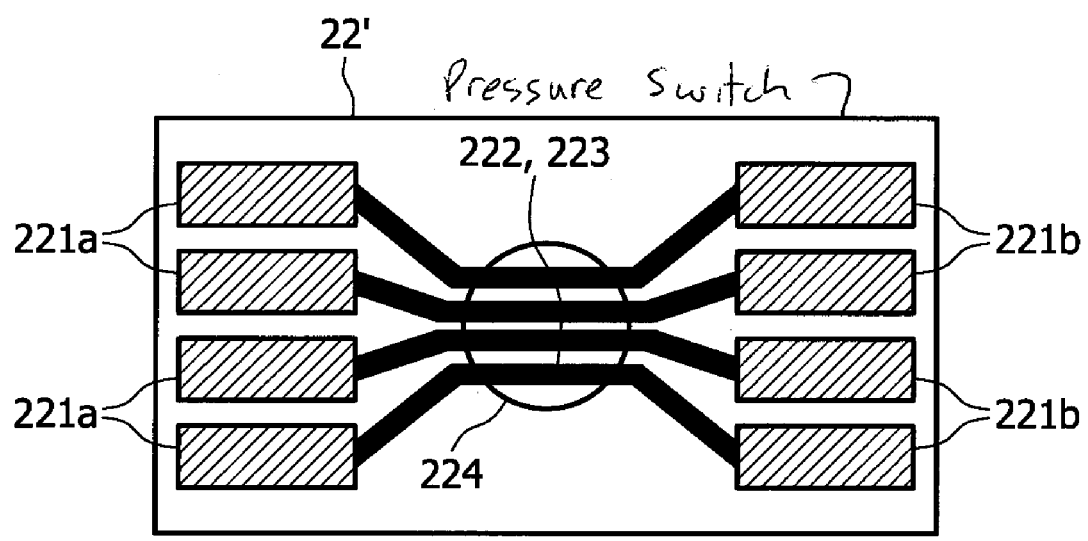
FIG. 4 shows a second embodiment of a switching unit in a top view.

FIG. 4 shows a second embodiment of a pressure switch 22' in a top view. This switch is provided for simultaneously switching four electrically conductive links or lines or cables 21 (not indicated). Correspondingly, the pressure switch 22' comprises four pairs of each a first and a second soldering pad 221a, 221b which again are provided for fixing adjacent segments or sections of the links or lines or cables 21 to be connected and disconnected, respectively.

Furthermore, the pressure switch 22' comprises four levers 222 and four counter contacts 223, wherein each one lever and counter contact is provided for connecting and disconnecting each one pair of a first and a second contact pads 221a, 221b as indicated in FIG. 3.

The four levers 222 are again pretensioned and actuated by the pressurized medium as explained above and are separated from the pressurized medium by means of one flexible membrane 224 which bulges against the levers 222 when the medium is pressurized.

As indicated above, the pressure switch 22' can be provided either such that by exerting a pressure via the pressurized medium the levers 222 are lifted from the counter contacts 223 so that the pressure switch 22' is opened as indicated in FIG. 3 or, in order to enhance safety of the transmission path 2 in case of a loss of pressure, the levers are brought into a contact-closed position by the pressure and are pretensioned into a contact-open position.

Pressure switches for simultaneously switching two, three or more than four electrically conductive links or lines 21 can be provided accordingly.

An example for a transmission path 2 with a single lead or line 21 is a unipolar cardiac pacing electrode or an RF power line for RF ablation in a catheter. An example for a transmission path 2 with a dual lead or line 21 is a coaxial cable within an MR catheter for active catheter localization. An example for a transmission path 2 with a multi channel connection lead or line 21 is an electrophysiological catheter with multiple mapping electrodes.

The pressure switches 22, 22' have to be selected such that they offer a sufficient electrical strength in dependence on the voltages and currents which are to be transmitted over the electrically conductive link or line 21. If necessary, the contact space surrounding the lever 222 and counter contact 223 is filled with a gas in order to increase the flash-over voltage of the switches for high power transmission. The switches have also to be selected or designed such that they provide a low open capacitance. The switches are preferably fabricated in microsystems technology in order to achieve the required level of miniaturization.

The distances between two adjacent pressure switches 22, 23, 24, . . . along the conductive link or line 21 are substantially arbitrary and are chosen in dependence on the proposed application of the transmission path 2 and especially the frequency of electrical or magnetic fields to which the path 2 is exposed such, that the line segments or sections 251; 252 between two adjacent switches 22; 23 remain safe with respect to RF induced resonances and corresponding heating by standing waves.

One of the main advantages of the transmission path 2 according to the invention is that the pressure switches 22, 23, 24, . . . and the pressure tube 25 or another lead function for operating the switches is not affected by surrounding electric or magnetic fields.

Finally, the transmission path 2 according to the invention can advantageously be used especially for connecting those electrical units which need long electrical leads 21 and/or which vary with respect to the frequency and the power level of the signals that are transmitted via the electrically conductive lead or line 21, like many types of implantables (e.g. neurostimulators, pacemakers, internal cardioverters and defibrillators) and interventional devices (e.g. active catheters for fast localization, electrophysiology catheters for endocardial ECG mapping and RF ablation).

While the invention has been illustrated and described in detail in the drawings and foregoing description, such illustration and description are to be considered illustrative or exemplary and not restrictive, and the invention is not limited to the disclosed embodiments.

The invention claimed is:

1. An RF safe transmission path for electrically connecting a first and a second electrical unit with each other, for use in an RF electrical and/or magnetic field, comprising:
    at least one electrically conductive link or connection lead or cable or line being subdivided into at least two line segments or sections which are connected to each other by means of at least one switching unit such that the line segments or sections remain RF safe with respect to RF induced resonances and corresponding heating by standing waves on the conductive link or connection lead or cable or line,
    wherein the at least one switching unit comprises a switch with electrical contacts for electrically separating and connecting, respectively, the at least two line segments or sections of the conductive link or connection lead or cable or line, by opening and closing, respectively, the electrical contacts, for switching the RF safe transmission path between an RF safe mode and a signal transmission mode in which signals are transmitted over the conductive link or connection lead or cable or line.

2. The RF safe transmission path according to claim 1, wherein the at least one switching unit comprises a pressure switch for opening and/or closing the electrical contacts by means of a pressure exerted by a medium which is supplied to the switching unit.

3. The RF safe transmission path according to claim 2, comprising a non-metallic pressure tube which is fixed at and guided along the electrically conductive link or connection lead or cable or line, through which pressure tube the medium is supplied to the switching unit.

4. An RF safe transmission path according to claim 1, wherein the at least one switching unit is provided in the form of a bimetal or thermal switch for opening the electrical contacts in case of an increasing temperature of the conductive link or connection lead or cable or line.

5. An RF safe transmission path according to claim 1, wherein the at least one switching unit is provided in the form of an electrical relay which is supplied and/or controlled via an optical fiber for opening and/or closing the electrical contacts.

6. An RF safe transmission path according to claim 5, wherein the at least one switching unit comprises a detector or sensor for detecting an RF electrical and/or magnetic field strength or a temperature increase, and for opening the electrical contacts in case of an increased RF electrical and/or magnetic field or a temperature increase.

7. A connection or base unit for transmitting signals to and/or receiving signals from at least one distal or remote electrical unit and/or for supplying the at least one distal or remote electrical unit via an RF safe transmission path, wherein the connection or base unit comprises a controller for controlling at least one switching unit of the RF safe transmission path for opening and/or closing its electrical contacts, the RF safe transmission path for electrically connecting a first and a second electrical unit with each other, for use in an RF electrical and/or magnetic field, comprising:
at least one electrically conductive link or connection lead or cable or line being subdivided into at least two line segments or sections which are connected to each other by means of at least one switching unit such that the line segments or sections remain RF safe with respect to RF induced resonances and corresponding heating by standing waves on the conductive link or connection lead or cable or line,
wherein the at least one switching unit comprises a switch with electrical contacts for electrically separating and connecting, respectively, the at least two line segments or sections of the conductive link or connection lead or cable or line, by opening and closing, respectively, the electrical contacts, for switching the RF safe transmission path between an RF safe mode and a signal transmission mode in which signals are transmitted over the conductive link or connection lead or cable or line.

8. The connection or base unit according to claim 7, comprising at least one sensor for detecting an RF electrical and/or magnetic field strength or a temperature along or at the RF safe transmission path, and wherein the controller is provided for evaluating the signal of the at least one sensor and for controlling at least one of the switching units such that the electrical contacts are opened if the RF electrical and/or magnetic field strength or the temperature exceeds a predetermined value.

9. The connection or base unit according to claim 7, comprising a pressure transducer for operating at least one of the switching units which are provided in the form of each a pressure switch.

10. An MR compatible device for use in a MR imaging system, comprising a first and a second electrical unit and an RF safe transmission path, the RF safe transmission path for electrically connecting the first and the second electrical unit with each other, for use in an RF electrical and/or magnetic field and comprising:
at least one electrically conductive link or connection lead or cable or line being subdivided into at least two line segments or sections which are connected to each other by means of at least one switching unit such that the line segments or sections remain RF safe with respect to RF induced resonances and corresponding heating by standing waves on the conductive link or connection lead or cable or line,
wherein the at least one switching unit comprises a switch with electrical contacts for electrically separating and connecting, respectively, the at least two line segments or sections of the conductive link or connection lead or cable or line, by opening and closing, respectively, the electrical contacts, for switching the RF safe transmission path between an RF safe mode and a signal transmission mode in which signals are transmitted over the conductive link or connection lead or cable or line.

* * * * *